(12) United States Patent  
Nakajima

(10) Patent No.: US 7,682,341 B2
(45) Date of Patent: Mar. 23, 2010

(54) INDWELLING NEEDLE

(75) Inventor: Hiroaki Nakajima, Tokyo (JP)

(73) Assignee: Medikit Co., Ltd, Tokyo (JP)

( * ) Notice: Subject to any disclaimer, the term of this patent is extended or adjusted under 35 U.S.C. 154(b) by 0 days.

(21) Appl. No.: 11/269,590

(22) Filed: Nov. 9, 2005

(65) Prior Publication Data

US 2007/0106221 A1 May 10, 2007

(51) Int. Cl.
*A61M 5/178* (2006.01)

(52) U.S. Cl. .................................. 604/168.01

(58) Field of Classification Search .......... 604/19, 604/48, 93.01, 164.01, 164.08, 263, 264, 604/189, 164.06, 198, 168.01, 900
See application file for complete search history.

(56) References Cited

U.S. PATENT DOCUMENTS

| | | | | |
|---|---|---|---|---|
| 4,935,012 A * | 6/1990 | Magre et al. | ................. | 604/192 |
| 5,000,740 A * | 3/1991 | Ducharme et al. | ........... | 604/162 |
| 5,030,205 A * | 7/1991 | Holdaway et al. | ...... | 604/164.02 |
| 5,462,533 A * | 10/1995 | Daugherty | ............. | 604/164.01 |
| 5,620,008 A * | 4/1997 | Shinar et al. | ................. | 600/576 |
| 5,954,698 A * | 9/1999 | Pike | ....................... | 604/167.03 |
| 6,131,433 A * | 10/2000 | Nakada et al. | ............ | 72/370.21 |
| 6,156,010 A * | 12/2000 | Kuracina et al. | ........ | 604/168.01 |
| 6,342,047 B1 * | 1/2002 | Urakawa et al. | ............ | 604/264 |
| 6,375,897 B1 * | 4/2002 | Bachand | ...................... | 422/58 |
| 6,440,119 B1 * | 8/2002 | Nakada et al. | .............. | 604/506 |
| 6,475,191 B2 * | 11/2002 | Tamura et al. | ......... | 604/164.08 |
| 6,607,511 B2 * | 8/2003 | Halseth et al. | ......... | 604/164.08 |
| 6,616,631 B2 * | 9/2003 | Takagi et al. | ................ | 604/110 |
| 6,620,136 B1 * | 9/2003 | Pressly et al. | .......... | 604/164.08 |
| 6,638,254 B2 * | 10/2003 | Nakagami | .............. | 604/164.08 |
| 6,676,638 B2 * | 1/2004 | Takagi et al. | ........... | 604/167.03 |
| 6,695,814 B2 * | 2/2004 | Greene et al. | .......... | 604/164.08 |
| 6,706,159 B2 * | 3/2004 | Moerman et al. | ...... | 204/403.03 |
| 6,786,891 B2 * | 9/2004 | Hiejima | ................. | 604/164.01 |
| 6,840,912 B2 * | 1/2005 | Kloepfer et al. | ............. | 600/583 |
| 6,855,128 B2 * | 2/2005 | Swenson | ..................... | 604/110 |
| 6,905,483 B2 * | 6/2005 | Newby et al. | .......... | 604/164.08 |
| 6,969,376 B2 * | 11/2005 | Takagi et al. | ................ | 604/263 |
| 7,008,404 B2 * | 3/2006 | Nakajima | .................... | 604/158 |

FOREIGN PATENT DOCUMENTS

| | | |
|---|---|---|
| EP | 0 763 369 A | 3/1997 |
| GB | 2 375 053 A | 11/2002 |
| JP | 2002-102347 A | 4/2002 |

* cited by examiner

*Primary Examiner*—Nicholas D Lucchesi
*Assistant Examiner*—Theodore J Stigell
(74) *Attorney, Agent, or Firm*—Smith Patent Office

(57) ABSTRACT

An indwelling needle is provided with an inner needle hub; an inner needle fixedly supported by the inner needle hub; a cover configured to cover the inner needle after use; and a flexible blood monitor being absorptive to blood, an end of which is linked with the inner needle hub.

10 Claims, 3 Drawing Sheets

INDWELLING NEEDLE

BACKGROUND OF THE INVENTION

1. Field of the Invention

The present invention relates to an indwelling needle for an infusion set, which has a down-sized constitution and is capable of regulating the amount of a blood back-flow.

2. Description of the Related Art

Indwelling needles are used to infuse various medicinal fluids into vascular systems. In some case, an indwelling needle is provided with an inner needle for being stuck into a vascular system and an outer needle coaxially fit on the inner needle. After sticking, the inner needle may be extracted but the outer needle is left inserted and used for infusion.

Japanese Patent Application Laid-open JP2002-102347 discloses an art of an indwelling needle assembly provided with a needle cover and blood monitoring means. The needle cover is configured to cover the inner needle and the blood monitoring means and hence assures safe disposal thereof without accidental sticking after use. The blood monitoring means is movably housed in the needle cover and provided with a chamber for receiving back-flow of blood. When the inner needle is inserted in the vascular system, an operator can observe the back-flow of the blood pooled in the chamber from the exterior so as to verify the inner needle is regularly inserted in the vascular system.

SUMMARY OF THE INVENTION

The chamber of the blood monitoring means needs to keep receiving the back-flow of the blood over a considerable period of time and is hence necessary to have a considerable capacity. Therefore the blood monitoring means necessarily has considerable dimensions. Further the cover needs to have enough dimensions to cover such blood monitoring means. It gives rise to a problem that increase in size of the indwelling needle is inevitable. Such increase in size results in operator's disadvantage in view of easiness of delicate handling and operation in practical use.

The present invention has been carried out in view of the above problem and is intended for providing an indwelling needle for an infusion set, which has a down-sized constitution and is capable of regulating the amount of a blood back-flow.

According to an aspect of the present invention, an indwelling needle is provided with an inner needle hub; an inner needle fixedly supported by the inner needle hub; a cover configured to cover the inner needle after use; and a flexible blood monitor being absorptive to blood, an end of which is linked with the inner needle hub.

Preferably, the blood monitor is configured to regulate the quickness of the spread of the blood. More specifically, the indwelling needle is further provided with a plug configured to fix the blood monitor with the inner needle hub, which is capable of regulating the tightness of fixation of the blood monitor with the inner needle hub so as to regulate the quickness of the spread of the blood.

More preferably, the blood monitor is formed to be of a long and thin string shape.

Further preferably, the cover is capable of expanding. More specifically, the cover is composed of an outer cylinder and an inner cylinder. The inner cylinder is movably housed in the outer cylinder and detachably supports the inner needle hub. Still preferably, the indwelling needle is further provided with an elastic member configured to keep repulsive force to separate the inner cylinder and the inner needle hub. Still preferably, the indwelling needle is further provided with a latch piece configured to lock the inner cylinder and the inner needle hub in an immovable state relative to the outer cylinder.

DETAILED DESCRIPTION OF THE PREFERRED EMBODIMENT

Throughout the specification, claims and the drawings, distal ends of constituent members are defined as ends directed to where a needlepoint points and proximal ends are defined as ends opposed thereto.

Figure 1:
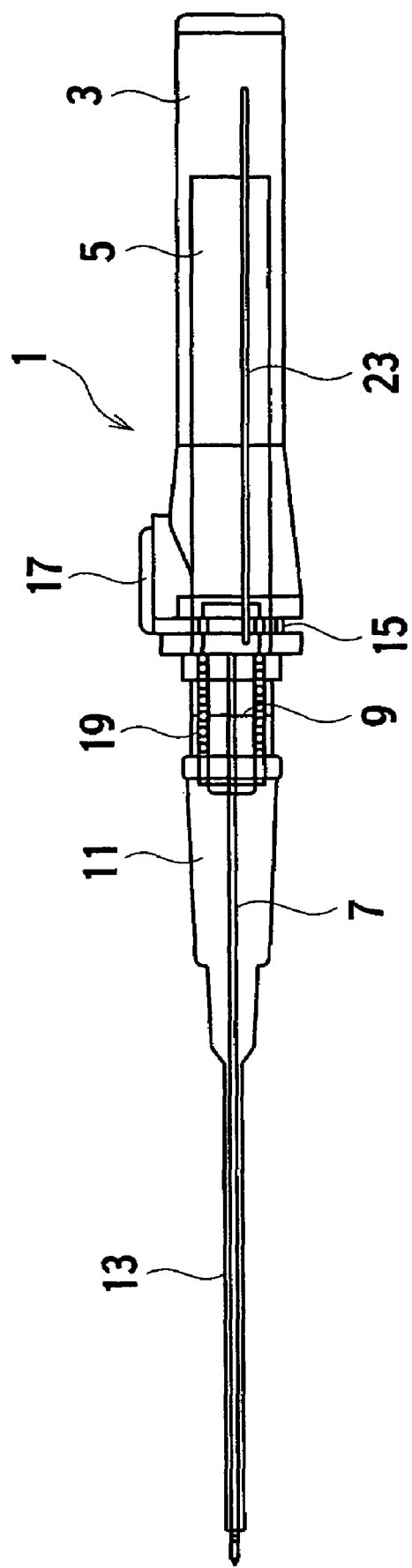
FIG. 1 is a schematic drawing schematically illustrating a state before use of an indwelling needle in accordance with an embodiment of the present invention.
Figure 2:
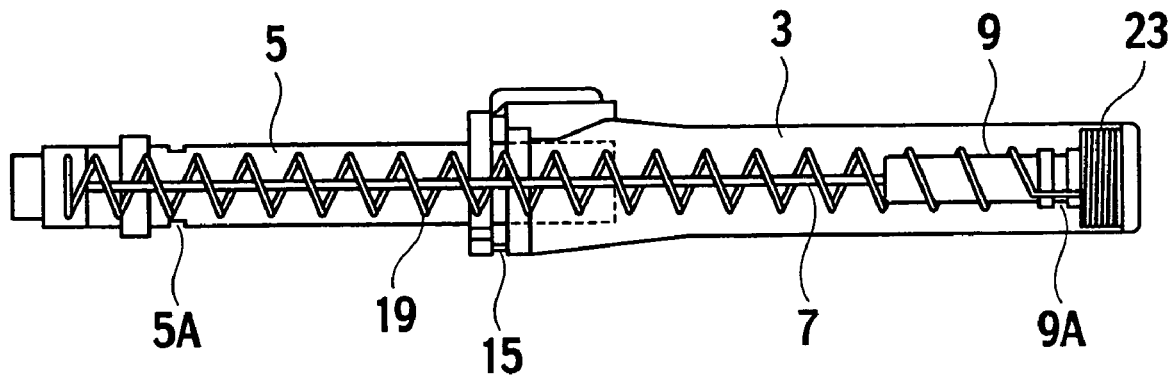
FIG. 2 is a schematic drawing schematically illustrating a state subject for disposal after use of the indwelling needle.

Referring to FIG. 1, an indwelling needle 1 in accordance with an embodiment of the present invention is provided with a transparent outer cylinder 3 having an opened distal end and a closed proximal end. The outer cylinder 3 is made of polycarbonate or any other transparent synthetic resin to allow visual observation of the interior. An inner cylinder 5 is housed in the outer cylinder 3 and axially movable relative to the outer cylinder 3 so as to project therefrom as shown in FIG. 2. A distal end of the inner cylinder 5 detachably supports an inner needle hub 9. An inner needle 7, which is formed to be sharp-pointed for being stuck into a patient body, is fixedly supported by the inner needle hub 9. An outer needle hub 11 is detachably fit on a distal end of the inner needle hub 9 and supports a proximal end of an outer needle 13. The outer needle 13 is formed to be tubular and the inner needle 7 is inserted and slidably fit therein.

The outer cylinder 3 is provided with an operation member 17 near the distal end thereof. The operation member 17 is provided with an annular latch piece 15, which is movable in a direction perpendicular to the axis of the outer cylinder 3. The latch piece 15 is configured to lock the inner cylinder 5 and the inner needle hub 9 so as to be in an immovable state before use of the indwelling needle 1.

More specifically, a lower part of the inner cylinder 5 is partly cut out to form a latching recess portion 5A as shown in FIG. 2 and the inner needle hub 9 is provided with a latching recess portion 9A in the vicinity of the proximal end thereof. The latching recess portion 5A and the latching recess portion 9A are so dimensioned as to be aligned in the axial direction in a state before use as shown in FIG. 1. The latch piece 15 latches with the latching recess portion 5A and further goes through the latching recess portion 5A to latch with the latching recess portion 9A in the state before use, thereby the latch piece 15 locks the inner cylinder 5 and the inner needle hub 9 so as to be in the immovable state before use.

An elastic member 19 such as a coil spring is installed in the inner cylinder 5 to span an inner surface of the distal end of the inner cylinder 5 and the inner needle hub 9. In the state before use, the elastic member 19 is compressed as shown in FIG. 1 and hence keeps repulsive force to separate the inner cylinder 5 and the inner needle hub 9, though the latch piece 15 locks the inner cylinder 5 and the inner needle hub 9. In a case where the operation member 17 is pressed, the latch piece 15 is released from the latching recess portion 5A and the latching recess portion 9A, then the elastic member 19 expands by means of the repulsive force so that the inner cylinder 5 projects out of the outer cylinder 3 and the inner needle hub 9 recedes toward the proximal end of the outer cylinder 3.

Then the projecting inner cylinder 5 covers a distal portion of the inner needle 7 and the outer cylinder 3 covers a proximal portion of the inner needle 7 as shown in FIG. 2. More specifically, the inner cylinder 5 and the outer cylinder 3 cooperatively function as a cover capable of expanding and contracting and configured to cover the inner needle 7 after use.

Figure 3:
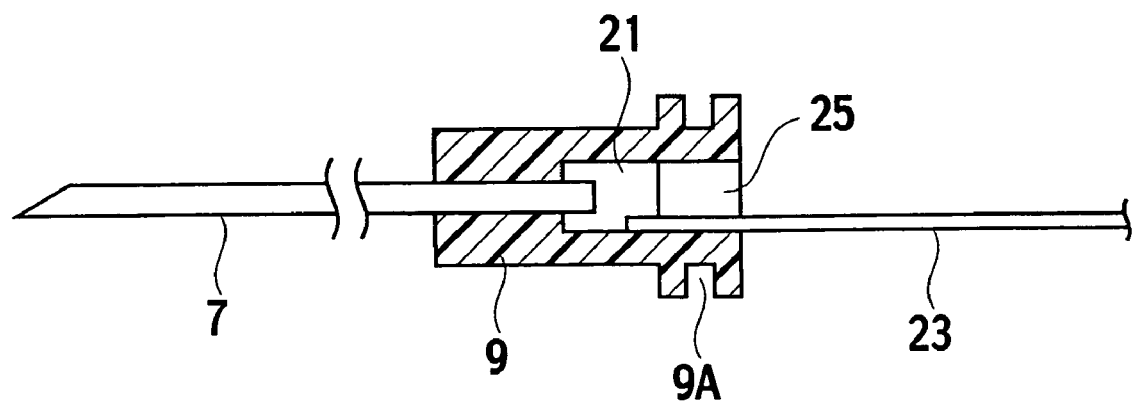
FIG. 3 is a schematic drawing schematically illustrating a state before use of an inner needle and a blood monitor.

Referring to FIG. 3, the inner needle hub 9 is provided with a small chamber 21 having an opening at the proximal end thereof. An end of a blood monitor 23, which is made to be of a long and thin string shape, of a line or of a fiber, is inserted into the chamber 21 and fixed by a plug 25 for closing the opening of the chamber 21. The opening of the chamber 21 may be tapered so that tightness of the fixation of the blood monitor 23 with respect to the opening can be regulated by means of regulation of insertion length of the plug 25.

The blood monitor 23 is made to be absorptive and flexible. Although any material having absorptive capacity and flexibility may be applied thereto, the blood monitor 23 is preferably made of any absorptive and flexible material such as felt, cloth or paper of pulp, cotton or any absorptive resin. More preferably the blood monitor 23 has a core made of such a material and flexible laminates thereon. Thereby the blood monitor 23 allows back-flow of blood to spread out of the chamber 21 when the indwelling needle 1 is inserted into a patient body. Quickness of spread of the blood may be regulated in advance by means of the tightness of the fixation of the blood monitor 23 by the plug 25.

In accordance with the above described constitution, in a case where the inner cylinder 5 and the inner needle hub 9 are fixed by means of the latch piece 15 as shown in FIG. 1, the blood monitor 23 is in a state of linearly expanding as shown in FIG. 3. When the needle is inserted into a vascular system of a patient, back-flow of blood flows into the chamber 21 of the inner needle hub 9.

Then the blood spreads through the blood monitor 23 to the exterior. Therefore regularity of insertion of the needle into the vascular system can be verified by means of observation of the back-flow of the blood and the quickness thereof. After verifying the regularity of the needle insertion into the vascular system, the operation member 17 is operated so as to cancel fixation of the inner cylinder 5 and the inner needle hub 9. Then the repulsive force of the elastic member 19 pull the inner needle 7 out of the outer needle 13 and push the inner cylinder 5 to project from the outer cylinder 3.

Figure 4:
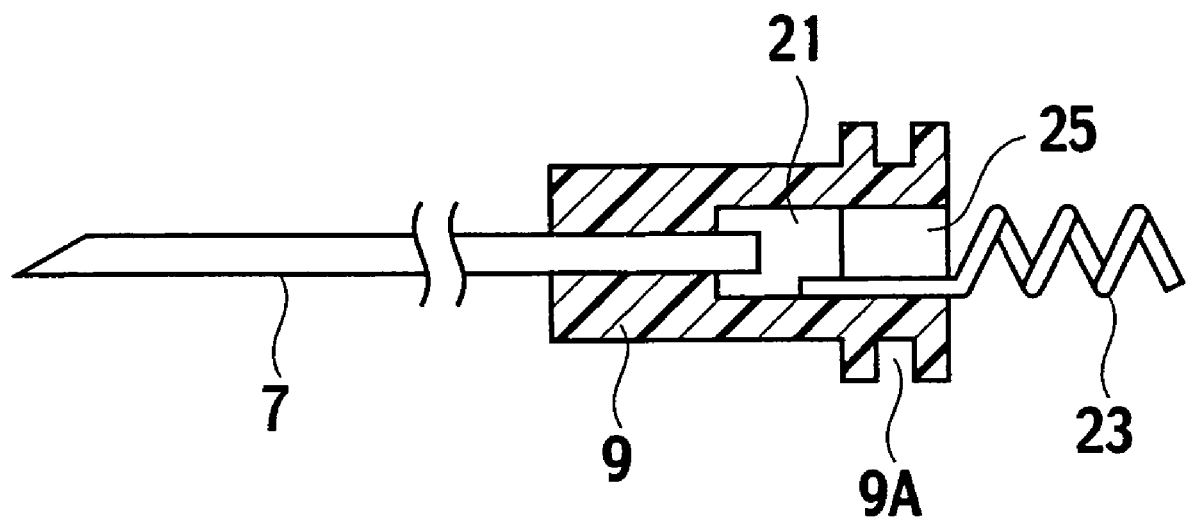
FIG. 4 is a schematic drawing schematically illustrating a state subject for disposal after use of the inner needle and the blood monitor.

As the inner needle 7 goes out of the outer needle 13 and the inner cylinder 5 projects from the outer cylinder 3, the blood monitor 23 is bent and folded between the proximal end of the outer cylinder 3 and the inner needle hub 9 as shown in FIGS. 2 and 4. When the inner cylinder 5 completely projects, the distal end of the inner cylinder 5 reaches ahead of the distal end of the inner needle 7. Thereby the distal end of the inner needle 7 is covered with the inner cylinder 5 so as to assure safety. It can be safely subject to disposal without accidental sticking. The total length of the outer cylinder 3 and the inner cylinder 5 projecting therefrom is not required to be so greater than the length of the inner needle 7. Therefore the total length at a time of disposal can be made relatively short.

Regularity of insertion of the needle into the vascular system can be verified by means of observation of spread of the blood through the string-like blood monitor 23, thereby there is no need to give considerable dimensions to the chamber 21. The chamber 21 can be small-sized as long as the dimensions of the chamber 21 are enough to connect the proximal end of the inner needle 7 with the blood monitor 23. Therefore the inner needle hub 9 may be made smaller in diameter and shorter in length, thereby the indwelling needle 1 may be made thinner and shorter. It leads to facility in handling and sticking of the indwelling needle 1.

Moreover, in accordance with the aforementioned constitution, because quickness of spread of the blood can be regulated by means of the tightness of the fixation of the blood monitor 23, loss of blood of the patient may be suppressed.

The contents of Japanese Patent Application No. 2004-143931 (filed May 13, 2004) are incorporated herein by reference in its entirety.

Although the invention has been described above by reference to a certain embodiment of the invention, the invention is not limited to the embodiments described above. Modifications and variations of the embodiment described above will occur to those skilled in the art, in light of the above teachings.

What is claimed is:

1. An indwelling needle comprising:
   an inner needle hub;
   an inner needle fixedly supported by the inner needle hub;
   a cover configured to cover the inner needle after use; and
   a flexible blood monitor being absorptive to blood and including one selected from the group consisting of a string, a line and a fiber, the blood monitor having an end linked with the inner needle hub and extending from the inner needle hub,
   wherein the cover comprises an outer cylinder and an inner cylinder, the inner cylinder being axially movably housed in the outer cylinder and detachably supporting the inner needle hub so that the inner cylinder is capable of projecting out of the outer cylinder and the inner needle is capable of receding into the outer cylinder.

2. The indwelling needle of claim 1, further comprising:
   an elastic member configured to keep repulsive force to separate the inner cylinder and the inner needle hub.

3. The indwelling needle of claim 2, further comprising:
   a latch piece configured to lock the inner cylinder and the inner needle hub in an immovable state relative to the outer cylinder.

4. The indwelling needle of claim 1, wherein the blood monitor takes a first position at which the blood monitor extends through the inner cylinder and beyond one end of the inner cylinder and a second position at which the blood monitor is disposed adjacent to one end of the outer cylinder in a reduced length from an original size.

5. An indwelling needle comprising:
   an inner needle hub;
   an inner needle fixedly supported by the inner needle hub;
   a cover configured to cover the inner needle after use;
   a flexible blood monitor being absorptive to blood and including one selected from the group consisting of a string, a line and a fiber, the blood monitor having an end linked with the inner needle hub and extending from the inner needle hub; and
   a plug configured to fix the blood monitor with the inner needle hub, the plug fixedly located inside of and at a proximal end of the inner needle hub, the plug being capable of regulating the tightness of fixation of the blood monitor with the inner needle hub so as to regulate the quickness of the spread of the blood,
   wherein the cover comprises an outer cylinder and an inner cylinder and wherein the blood monitor takes a first position at which the blood monitor extends through the inner cylinder and beyond one end of the inner cylinder and a second position at which the blood monitor is disposed adjacent to one end of the outer cylinder in a reduced length from an original size.

6. The indwelling needle of claim 5, wherein the cover is capable of expanding.

7. An indwelling needle comprising:

an inner needle hub;

an inner needle fixedly supported by the inner needle hub;

a cover configured to cover the inner needle after use; and a flexible blood monitor being absorptive to blood and including one selected from the group consisting of a string, a line and a fiber, the blood monitor having an end linked with the inner needle hub and extending from the inner needle hub, line and a fiber, the blood monitor having an end linked with the inner needle hub and extending from the inner needle hub, wherein the cover comprises an outer cylinder and an inner cylinder, the inner cylinder being axially movably housed in the outer cylinder and detachably supporting the inner needle hub so that the inner cylinder is capable of projecting out of the outer cylinder and the inner needle is capable of receding into the outer cylinder, and wherein the flexible blood monitor extends through the inner cylinder and beyond a proximal end of the inner cylinder.

8. The indwelling needle of claim 7, further comprising:

an elastic member configured to keep repulsive force to separate the inner cylinder and the inner needle hub.

9. The indwelling needle of claim 7, further comprising:

a latch piece configured to lock the inner cylinder and the inner needle hub in an immovable state relative to the outer cylinder.

10. The indwelling needle of claim 7, wherein the blood monitor takes a first position at which the blood monitor extends through the inner cylinder and beyond one end of the inner cylinder and a second position at which the blood monitor is disposed adjacent to one end of the outer cylinder in a reduced length from an original size.

* * * * *